United States Patent
Pasricha

(12) 
(10) Patent No.: US 8,560,053 B2
(45) Date of Patent: Oct. 15, 2013

(54) METHODS AND APPARATUSES FOR ENDOSCOPIC RETROGRADE CHOLANGIOPANCREATOGRAPHY

(75) Inventor: Pankaj Jay Pasricha, Cupertino, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 283 days.

(21) Appl. No.: 12/843,001

(22) Filed: Jul. 23, 2010

(65) Prior Publication Data

US 2011/0028833 A1 Feb. 3, 2011

Related U.S. Application Data

(60) Provisional application No. 61/231,007, filed on Aug. 3, 2009.

(51) Int. Cl.
*A61B 6/00* (2006.01)
*A61B 1/00* (2006.01)

(52) U.S. Cl.
USPC .......................................... 600/431; 600/104

(58) Field of Classification Search
USPC ..................... 600/407, 431, 104, 114; 604/28
See application file for complete search history.

(56) References Cited

U.S. PATENT DOCUMENTS 4,781,677 A * 11/1988 Wilcox ........................... 604/28
5,562,099 A * 10/1996 Cohen et al. ................. 600/458

OTHER PUBLICATIONS

"ERCP (Endoscopic Retrograde Cholangiopancreatography)", Nov. 2004, pp. 1-3, NIH Publication No. 05-4336, The National Digestive Diseases Information Clearinghouse (NDDIC).
Amber J. Tresca, "Endoscopic Retrograde Cholangiopancreatography (ERCP)", Jan. 18, 2008, pp. 1-2, About.com.

* cited by examiner

*Primary Examiner* — Michael Rozanski

(57) ABSTRACT

A method is disclosed for distending a body lumen in the performance of endoscopic retrograde cholangiopancreatography (ERCP). The method comprises insufflating the body lumen with contrast agent to distend the body lumen. The contrast agent includes gas.

13 Claims, 8 Drawing Sheets

METHODS AND APPARATUSES FOR ENDOSCOPIC RETROGRADE CHOLANGIOPANCREATOGRAPHY

CROSS-REFERENCE TO RELATED APPLICATIONS

This application claims priority to U.S. provisional application Ser. No. 61/231,007, filed Aug. 3, 2009, which is incorporated by reference herein.

FIELD OF THE INVENTION

The present invention relates to methods and apparatuses for endoscopic retrograde cholangiopancreatography.

BACKGROUND OF THE INVENTION

Endoscopic retrograde cholangiopancreatography (hereinafter "ERCP") is a common and valuable procedure for patients with a variety of disorders of the pancreas and biliary ducts such as inflammatory strictures, gallstones, leaks, cancer and other abnormalities. In ERCP, a conventional contrast agent (i.e., a dye) is injected into the biliary (also known as bile) and pancreatic ducts using a flexible video endoscope. Then X-rays (e.g., CAT scan) are taken to outline the biliary duct, pancreatic duct and pancreas. However, ERCP is a demanding procedure technically and carries significant risk for the patient. Some of these risks include, for example, pancreatitis or failure to adequately treat the underlying condition. These problems are due in part to the amount of manipulation required to freely canulate the desired target and in part to the pressure resulting from the contrast injection. In many cases, a patient may have a tortuous distal duct with its lumen completely occluded due to collapse of its walls. Currently this is best negotiated with a thin catheter or a slick wire. Repeated attempts at canulation and contrast injection may result in increased pressure, edema and inflammation of the major duodenal papilla (hereinafter "papilla"), causing partial obstruction which can impede canulation further or lead to pancreatitis.

Difficult canulation also can prompt a variety of increasingly aggressive maneuvers such as needle-knife papillotomy that can by themselves add to the risk of the ERCP procedure. Other adverse consequences include tissue infection which may occur when the contrast agent unavoidably dissects into surrounding tissue. Additional adverse consequences include fluorsoscopic exposure and the incorporation of additional "prophylactic" measures such as pancreatic stenting to prevent some of the complications from difficult canulation. Free canulation of the papilla is an essential prerequisite for adequate diagnostic and therapeutic maneuvers related to the procedure of ERCP.

Thus, it would be therefore desirable to offer a solution that would overcome the disadvantages of the procedure described above.

SUMMARY OF THE INVENTION

This invention comprises methods and apparatuses that are used to distend the biliary and pancreatic ducts for ERCP procedures.

A method is disclosed to distend the proximal and distalmost segments of the biliary and pancreatic ducts that uses an inert gas as a contrast agent to insufflate such ducts.

In one embodiment of the method, the inert gas may be carbon dioxide. An inert absorbable gas such as carbon dioxide is the ideal agent for insufflation as it will not create submucosal blebs and it will naturally track to even the smallest openings even if the tip of the catheter is not in perfect position. Further, carbon dioxide is well tolerated physiologically. Carbon dioxide can aid in X-ray visualization of the biliary and pancreatic duct without contrast. Alternatively, carbon dioxide may be used along with contrast. Carbon dioxide is absorbed quickly enough so that it will not interfere with subsequent contrast radiography of the duct if contrast is needed or desired. Other inert gases may be used. In addition, such gases may be enriched with other therapeutic or diagnostic agents.

In another embodiment, perfluorocarbon (PFC) may be used as a contrast agent to insufflate the proximal and distalmost segments of the billary and pancreatic ducts. PFC may be in the form of a gas or liquid or variably enriched with other therapeutic or diagnostic agents.

An apparatus is disclosed for distending the biliary and pancreatic ducts by insufflating the biliary and pancreatic ducts.

A method is disclosed to distend the biliary and pancreatic ducts that applies a vacuum to the papilla to open and distend the ducts.

An apparatus is disclosed for providing a vacuum to enable distention of the biliary and pancreatic ducts.

In accordance with an embodiment of the invention, a method is disclosed for distending a body lumen in performance of endoscopic retrograde cholangiopancreatography (ERCP), the method comprising insufflating the body lumen with contrast agent to distend the body lumen, the contrast agent including a gas.

In accordance with another embodiment of the invention, an apparatus is disclosed that is adapted to be delivered within a body in performance of endoscopic retrograde cholangiopancreatography (ERCP), the apparatus comprising a cannula including a lumen for passing a contrast agent through the lumen to insufflate a body lumen within the body and a wire lumen for passing a wire through the wire lumen and into the body lumen.

In accordance with another embodiment of the invention, a method is disclosed for distending a body lumen within a body in performance of endoscopic retrograde cholangiopancreatography (ERCP), the method comprising applying a vacuum to distend the body lumen to enable the performance of ERCP.

In accordance with yet another embodiment of the invention, an apparatus is disclosed that is adapted to be delivered within a body in performance of endoscopic retrograde cholangiopancreatography (ERCP), the apparatus comprising a cannula including a lumen for applying a vacuum to a body lumen within the body and a lumen for passing a wire therethrough and into the body lumen.

DETAILED DESCRIPTION OF THE INVENTION

Figure 1:
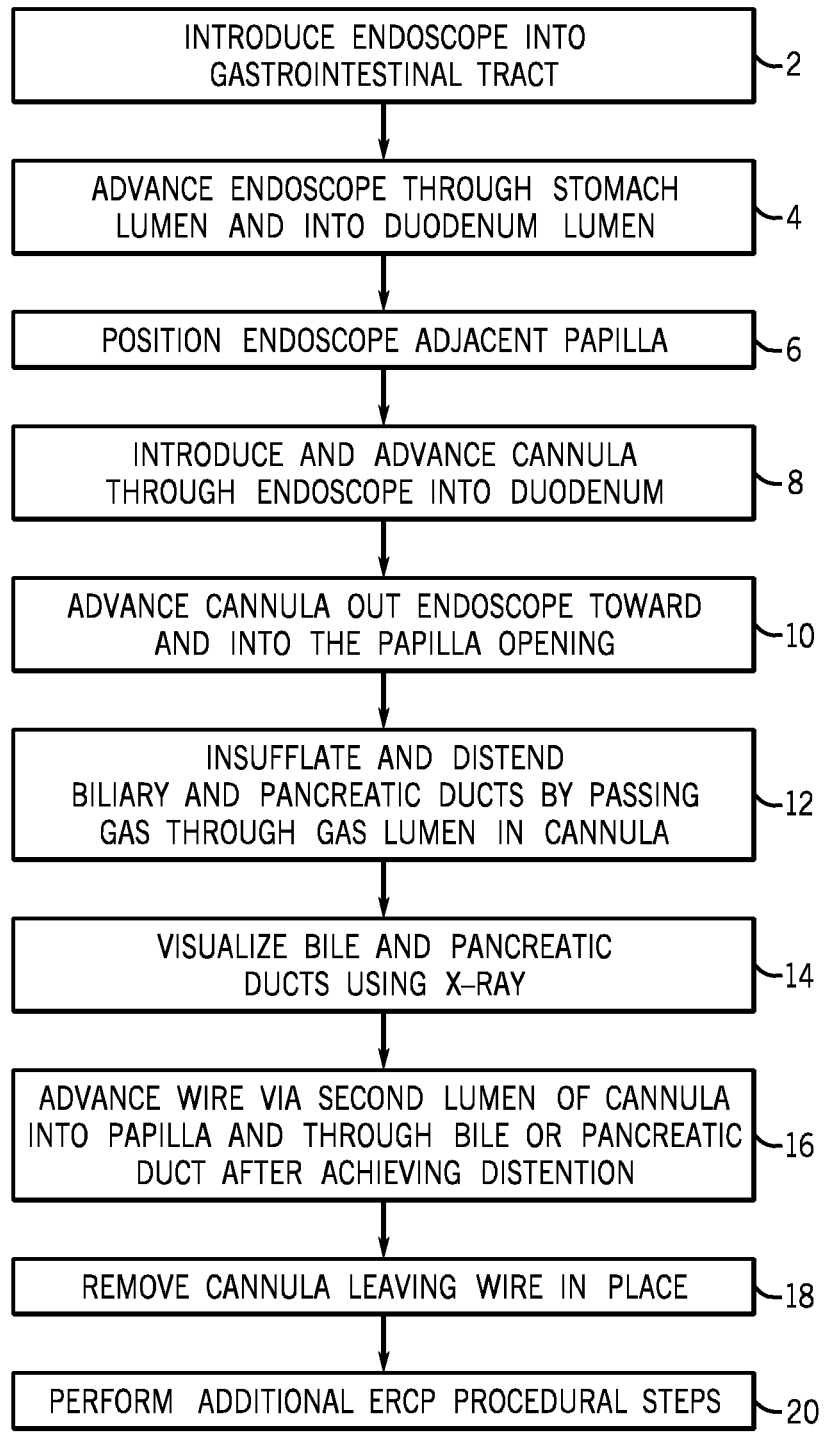
FIG. 1 depicts a block diagram of the steps of the method of distending the biliary and pancreatic ducts in the performance of ERCP by insufflating the biliary and pancreatic ducts in accordance with the present invention.
Figure 2:
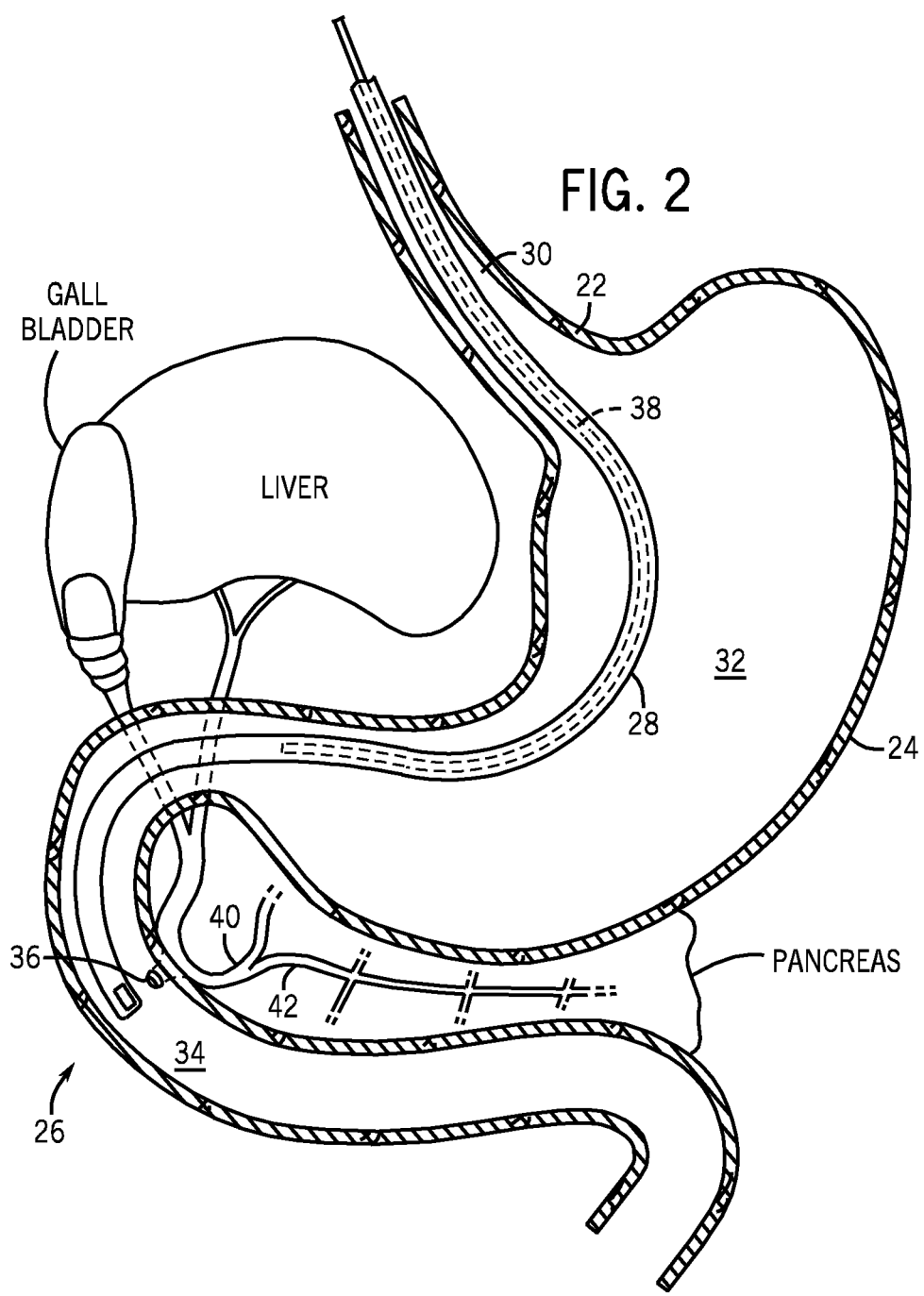
FIGS. 2, 3 and 4 depict cross-sectional schematic views of the gastrointestinal tract corresponding to the steps of the method depicted in FIG. 1.
Figure 3:
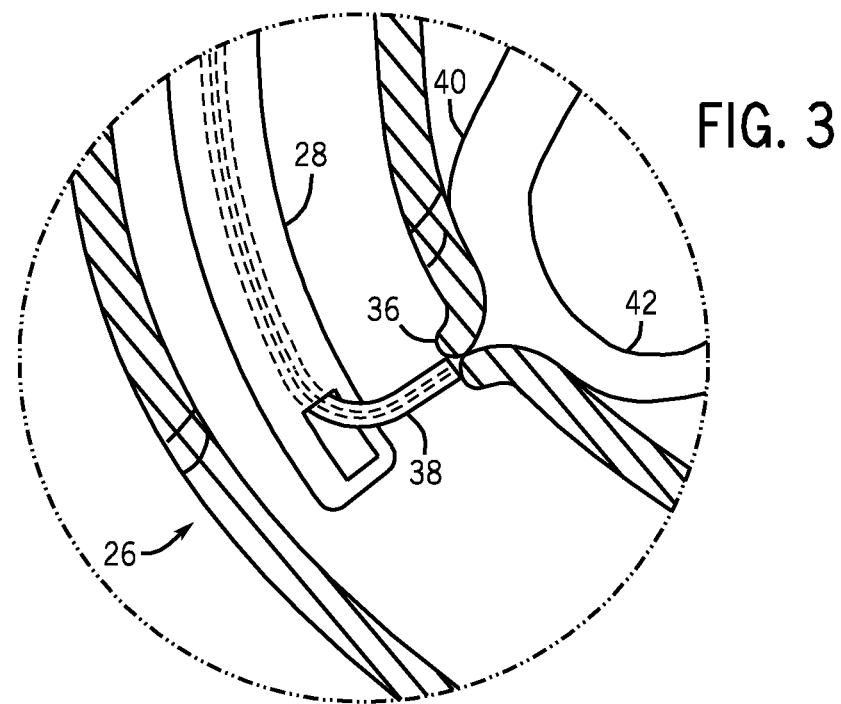
Figure 4:
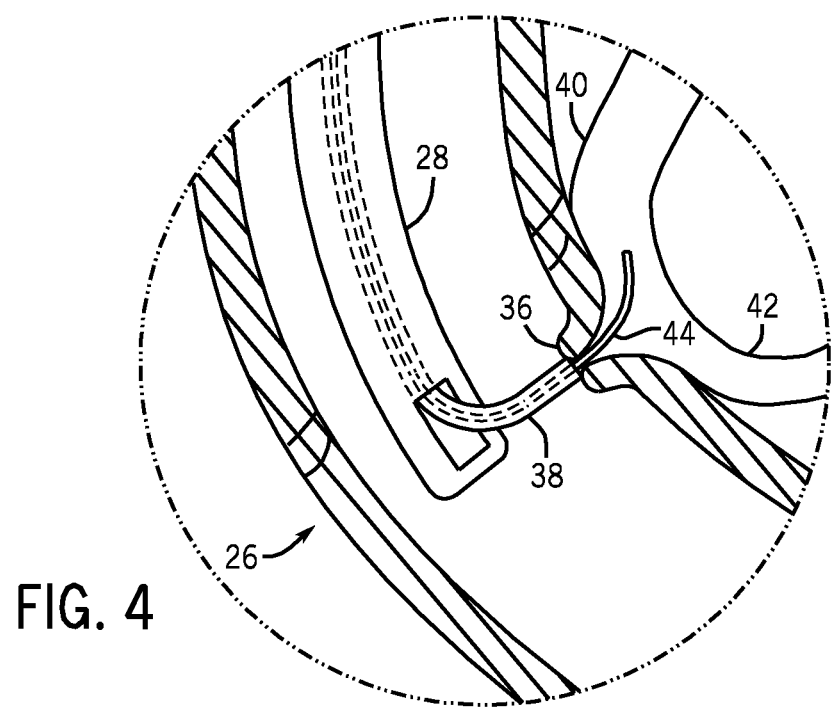

FIG. 1 depicts a block diagram of the steps of the method of distending the biliary and pancreatic ducts in the performance of ERCP (endoscopic retrograde cholangiopancreatography) by insufflating the biliary and pancreatic ducts in accordance with the present invention. FIGS. 2, 3 and 4 depict cross-sectional views of the gastrointestinal tract corresponding to the steps of the method depicted in FIG. 1, and as such, FIGS. 2, 3 and 4 will be discussed as they correspond to the steps of the method depicted in FIG. 1. In accordance with one illustrative embodiment, steps 2-20 are performed sequentially, but it will be clear to those skilled in the art, after reading this disclosure, how to make and use alternative embodiments of the present invention in which some of the steps 2-20 of the method are performed in a different order.

While describing the steps of the method in FIG. 1, reference is made to FIGS. 2, 3 and 4. Esophagus 22, stomach 24 and duodenum 26 of the gastrointestinal tract are shown in FIG. 2. At steps 2 and 4, the doctor will introduce a delivery apparatus such as endoscope 28 into a patient's mouth (not shown), and advance it down esophagus lumen 30 through stomach lumen 32, and into duodenum lumen 34. (Esophagus lumen 30, stomach lumen 32, and duodenum lumen 34 are all body lumens or cavities of the gastrointestinal tract.) Note, however, that only a portion of esophagus 22 is shown. Next, at step 6, the doctor will position endoscope 28 within duodenum lumen 34 adjacent papilla 36 (major duodenal papilla 36) along the wall of duodenum 26. Endoscope 28 may be a video endoscope to enable the doctor to visualize the subject area. However, a separate endoscope may be used for visualization or the procedure in FIG. 1 may be performed blindly.

As known to those skilled in the art, endoscope 28 has a lumen that extends from the proximal end (proximate the mouth) to a distal end thereof (proximate the delivery site) for receiving and advancing other endoscopic equipment.

At step 8, cannula 38 is actually introduced into and through a lumen in endoscope 22 for such advancement into the gastrointestinal tract. At step 10, the doctor continues to advance cannula 38 until distal end 38a of cannula 38 is advanced out of an opening in the distal end of endoscope 28 and into papilla 36. This is shown in FIG. 3.

Note that the steps of the method shown in FIG. 1 are described herein as being performed by one doctor, but one skilled in the art will know, after reading this disclosure, that one or more steps of this method may be performed by more than one doctor or medical professional (under the care and supervision of a doctor).

Now, following step 10, the doctor will insufflate papilla 36 with gas via the papilla opening to distend biliary duct 40 and pancreatic duct 42 at step 12. As described below, the gas is passed through a gas lumen within cannula 38 to achieve distention in the biliary and pancreatic ducts. In some cases, a doctor may continue to release a small amount of gas to maintain distention to enable the doctor to perform the remaining steps of the ERCP procedure. (The biliary and pancreatic ducts are body lumens within a body of a patient.)

The gas used for insufflation is preferably carbon dioxide as a contrast agent. Carbon dioxide is well tolerated physiologically. Carbon dioxide can aid in X-ray visualization of the biliary and pancreatic ducts without any need for a conventional contrast agent such as Hypaque solution (there are others conventional agents). Alternatively, carbon dioxide may be used prior to conventional contrast injection or along with a conventional contrast agent as a carrier of such conventional contrast agent. When used before conventional contrast agent injection, carbon dioxide is insufflated, and then a conventional contrast agent is injected into the ducts. In this respect, carbon dioxide is absorbed quickly enough so that it will not interfere with subsequent conventional contrast radiography of the duct when a conventional contrast agent is needed or desired.

When carbon dioxide is used as a carrier, however, carbon dioxide is used as a vehicle to carry vaporized conventional contrast agents. In this respect, the conventional contrast agents are converted into an aerosol. Reduction in the use of conventional contrast agents significantly reduces some of the risks to the patient (e.g., conventional contrast migration etc.). The injection of conventional contrast agent is discussed in more detail below with respect to step 20.

In another embodiment, perfluorocarbon (PFC) may be used in ERCP to insufflate the proximal and distal-most segments of the biliary and pancreatic ducts. PFC is unique in that it provides a safer contrast agent than conventional contrast agents. PFC may be in the form of a gas or liquid. PFC may be anti-inflammatory by itself or variably enriched with oxygen or other agents that can protect the pancreas against injury. These enriching agents may include anti-inflammatory compounds, local anesthetics, or other nerve blocking agents. However, PFC may be enriched with other therapeutic or diagnostic agents as known by those skilled in the art.

Those skilled in the art know that other gases, liquids or combinations of the above (including, e.g., fluorocarbons (FC), perfluorooctyl bromide (perflubron or PFOB)), may be used to achieve similar results.

At step 14, the doctor will use an X-ray machine (e.g., CAT scan) to take X-ray films to visualize biliary duct 40 and pancreatic duct 42 to determine medical abnormalities and to visualize the ducts and the region in general.

At step 16, the doctor will then advance (guide) wire 44 through a wire lumen within cannula 38 into the opening in papilla 36. Wire 44 will continue to be advanced into the biliary or pancreatic duct after distention is achieved (i.e., after the ducts become inflated). This is shown in FIG. 4. Wire 44 provides a robust and sustained access to the duct over which various accessories can be passed and exchanged as described below (step 20) with respect to the performance of the additional steps of the ERCP.

In some cases, wire 44 may be advanced into the ducts incrementally as the ducts become inflated. In this sense, the gas inflation aids in the advancement of wire 44.

At this point, cannula 38 is removed leaving wire 44 in place at step 18.

Following step 18, the doctor will perform additional ERCP steps of the procedure at step 20. For example, a catheter may be passed to inject conventional contrast or to collect bile or pancreatic juice for diagnostic purposes. Other examples of the steps of ERCP include passing a biopsy forceps or brush to obtain tissue for analysis, passing a catheter for pressure measurement, passing a small endoscope into the duct for passing a sphinterotome to cut the sphincter biliary, pancreatic or both), passing a stent to relieve obstruction in the biliary or pancreatic duct, passing a basket to crush and/or retrieve stones in the biliary or pancreatic duct, passing a balloon to dilate stricture or retrieve stones and/or advancing an ablation device to relieve the blockage. Other steps may be performed as well as known to those skilled in the art.

Figure 5A:
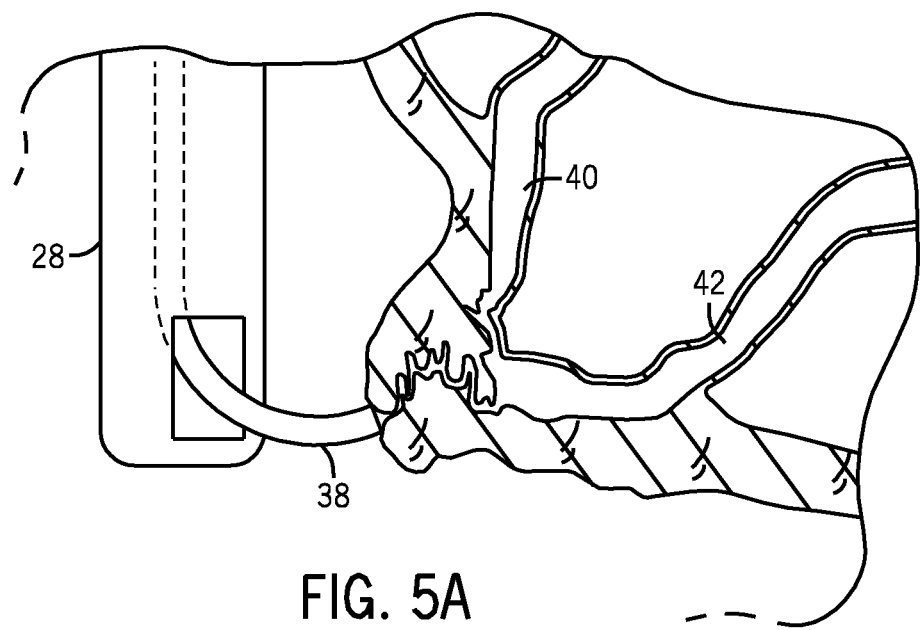
FIGS. 5A and 5B depict enlarged natural views of the biliary and pancreatic ducts of a patient before and after insufflation of the ducts.
Figure 5B:
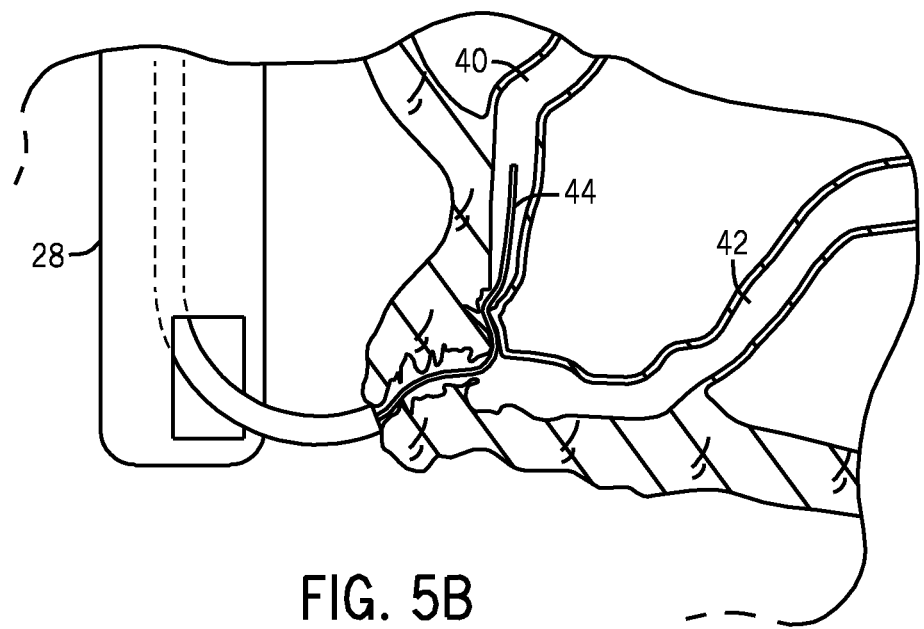

FIGS. 5A and 5B depict enlarged natural views of the biliary and pancreatic ducts of a patient before and after insufflation of the ducts, respectively. In particular, FIG. 5A illustrates a narrow and tortuous path connecting the biliary and pancreatic ducts. This tortuous path makes it difficult for a doctor to fill contrast agents into the ducts as well as advance a wire into the ducts. FIG. 5B illustrates distended biliary and pancreatic ducts after insufflation has been achieved. Note that a doctor may more easily advance wire 44 within the paths.

Figure 6A:
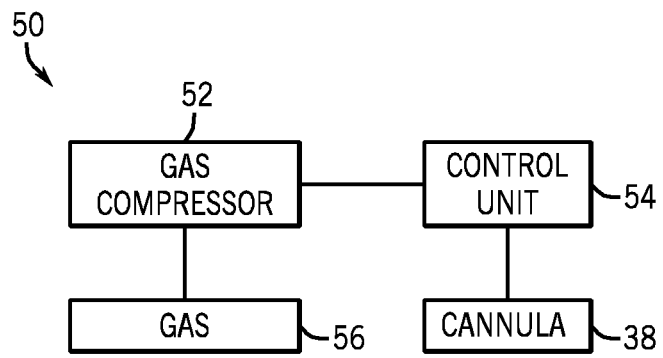
FIG. 6A depicts a block diagram of the components of an apparatus used for insufflating the biliary and pancreatic ducts.
Figure 6B:
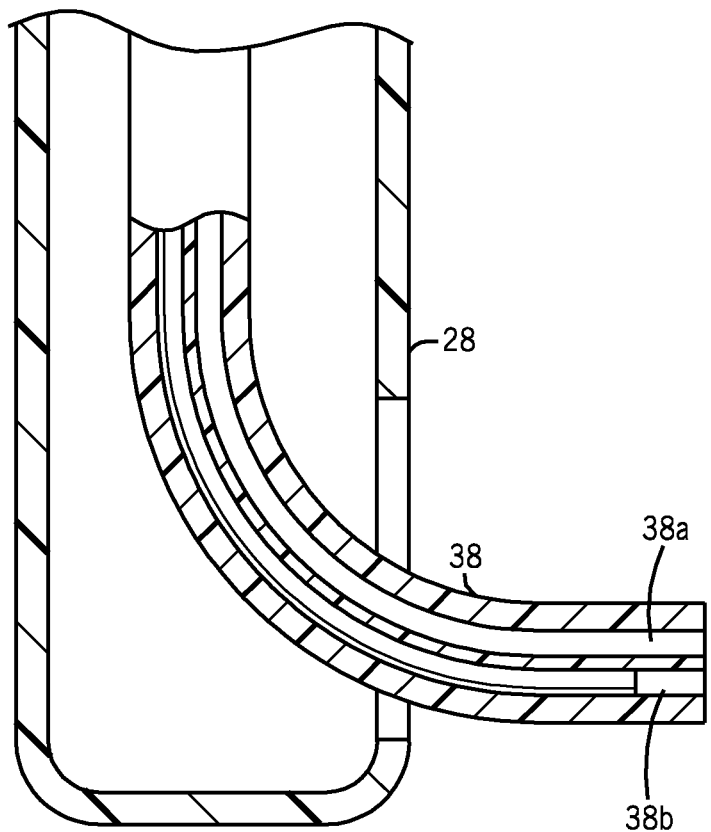
FIG. 6B depicts an enlarged view of the end of the cannula used for insufflating.

FIG. 6A depicts a block diagram of the components of an apparatus 50 used for insufflating the biliary and pancreatic ducts. FIG. 6B depicts an enlarged view of the end of cannula 38 used for insufflating.

In particular, apparatus 50 includes cannula 38, gas compressor 52 for providing compressed gas, control unit 54 operatively connected to compressor 52 and cannula 38 via control unit 54 for controlling the gas pressure through cannula 38 and gas supply 56 for supplying gas to gas compressor 52.

Gas compressor 52 includes conventional components known by those skilled in the art such as a gas pump and controls for starting and stopping the pump to maintain pressure in the tank, a pressure gauge and safety valve. Gas compressor 52 typically includes a tank for gas storage and delivery by cannula 38 as desired. Control unit 54 includes conventional electronic components as known by those skilled in the art (e.g., processor, memory, operating system and application software) to control gas (by way of a valve) delivered through the gas lumen in cannula 38. Apparatus 50 may optionally include water supply tank (not shown) operatively connected to air compressor 52 in the event the operator desires to supply water to the affected area. One skilled in the art knows, after reading this disclosure, that liquids, aerosols or combinations of gas and liquid may be used with similar type of equipment. For example, for an aerosol approach, a vaporizer similar in technology to conventional consumer vaporizer may be used or an aerosol compressor may be used as known to those skilled in the art. Note that control unit 54 may be activated by a hand or foot operated switch. FIG. 6B illustrates an enlarged view of the end of cannula 38 showing gas lumen 38a and wire lumen therein.

It will be known to those skilled in the art, after reading this disclosure, that cannula 38 may include several lumens (e.g., 38a, 38b) for delivering various materials or advancing various instruments for ERCP or other medical procedures. Those skilled in the art will also know, after reading this disclosure, that gas lumen 38a may be used for gas, liquid, aerosol or other combinations of contrast agents or other therapeutic agents (e.g., oxygen).

Figure 7:
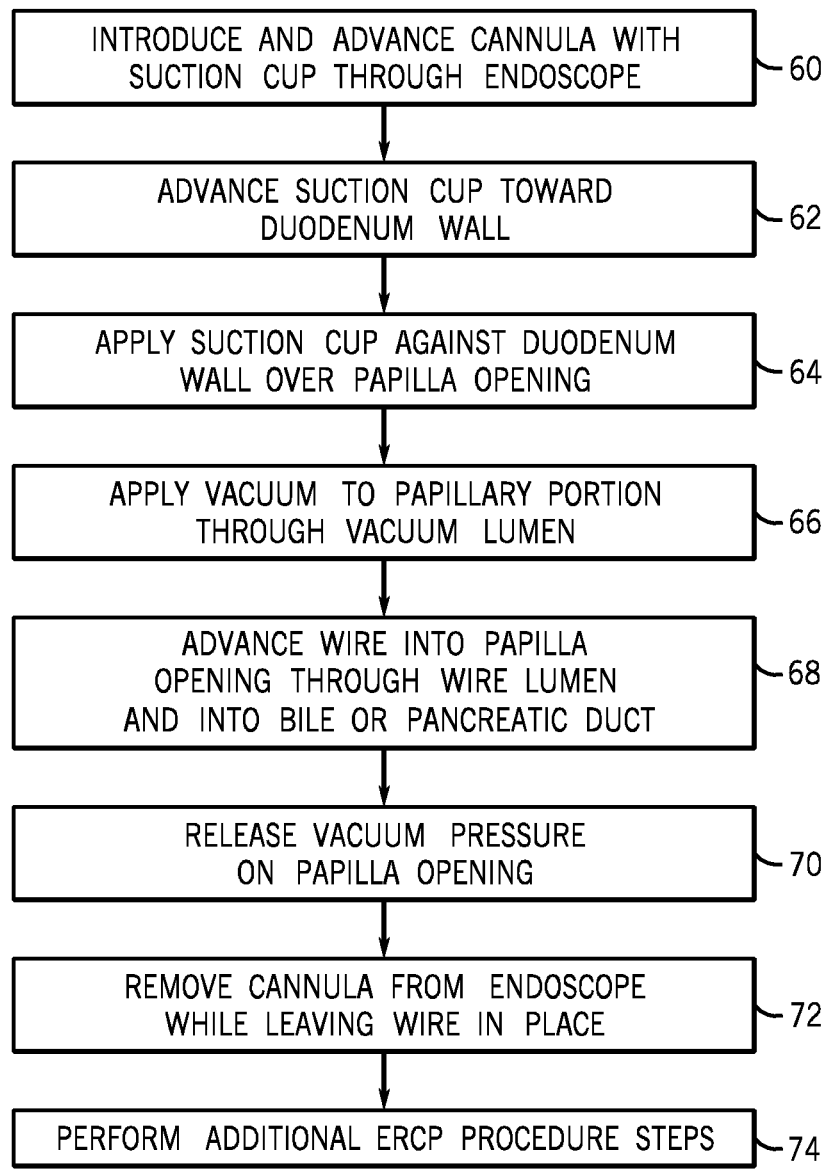
FIG. 7 depicts a block diagram of the steps of the method of distending the biliary and pancreatic ducts by applying a vacuum to the duodenal papilla in accordance with another embodiment of the present invention.

FIG. 7 depicts a block diagram of the steps of the method of distending the biliary and pancreatic ducts by applying a vacuum to the duodenal papilla in accordance with another embodiment of the present invention. The initial steps of the method in FIG. 7 are the same as steps 2-8 of the method depicted in FIG. 1. Therefore, these steps will not be discussed herein.

Figure 8A:
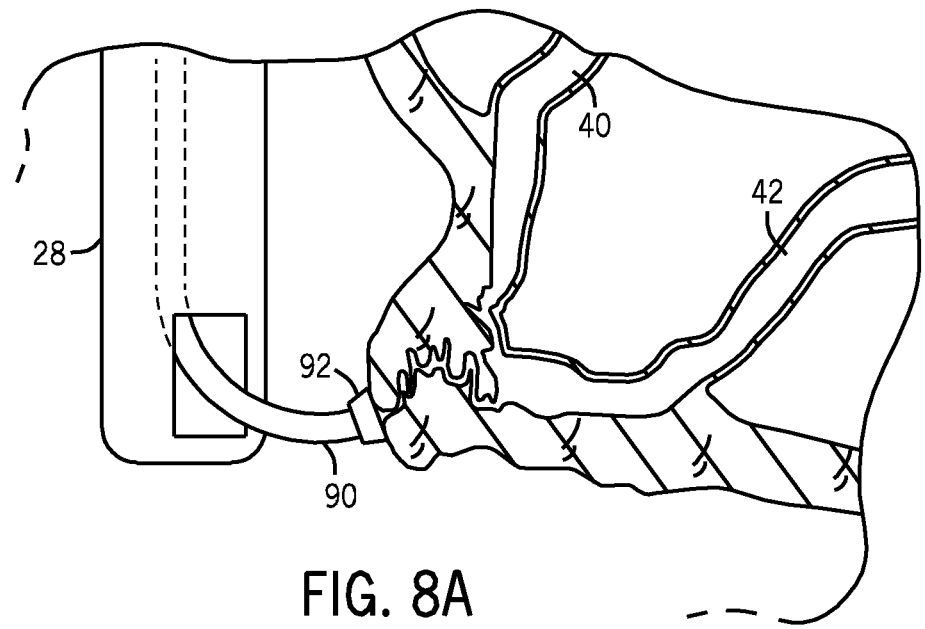
FIGS. 8A and 8B depict an enlarged natural view of the duodenal papilla and the biliary and pancreatic ducts of a patient before and after distension of the biliary and pancreatic ducts.

At step 60, the doctor will introduce and advance a cannula through endoscope 28. In this embodiment, cannula 90 will incorporate suction capability (suction cup 92 and related components) as described below with respect to FIGS. 8A, 8B, 9A and 9B. At step 62, the doctor will advance cannula 90 and suction cup 92 through endoscope toward duodenum wall adjacent papilla 36. At step 64, the doctor will manipulate the cannula 38 to apply suction cup 92 against the duodenum wall over papilla 36. That is, suction cup 92 will be applied gently against duodenum wall over papilla 36. FIG. 8A depicts the suction cup 92 in the proper position.

Figure 8B:
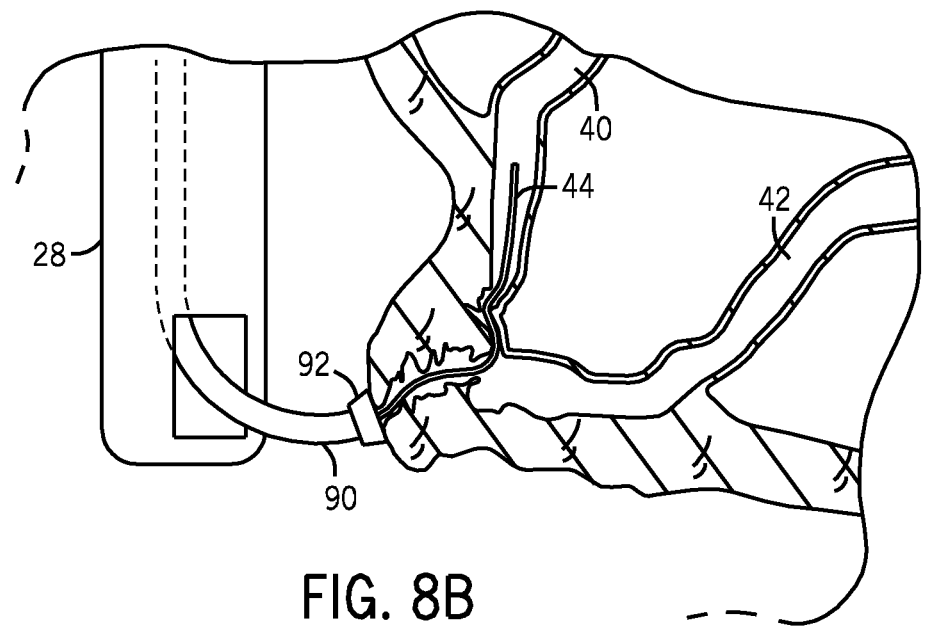

At step 66, a vacuum pressure will be applied to expand (i.e., distend) the common duct (papillary portion) of biliary and pancreatic ducts. At step 68, the doctor will advance wire 94 through a wire lumen within cannula 90 and through the distended path of the biliary and pancreatic ducts. The vacuum pressure is then released at step 70. In practice, a suck and release action will happened to allow the wire to pass through the ducts. A vacuum pressure of 40-60 cpm (cycles per minute) may be used for this purpose. FIG. 8B illustrates the distended ducts along with the advanced wired 94. Cannula 90 is then removed leaving wire 94 in place at step 72. At step 74, other ERCP steps are performed as described above with respect to the method of FIG. 1.

Figure 9A:
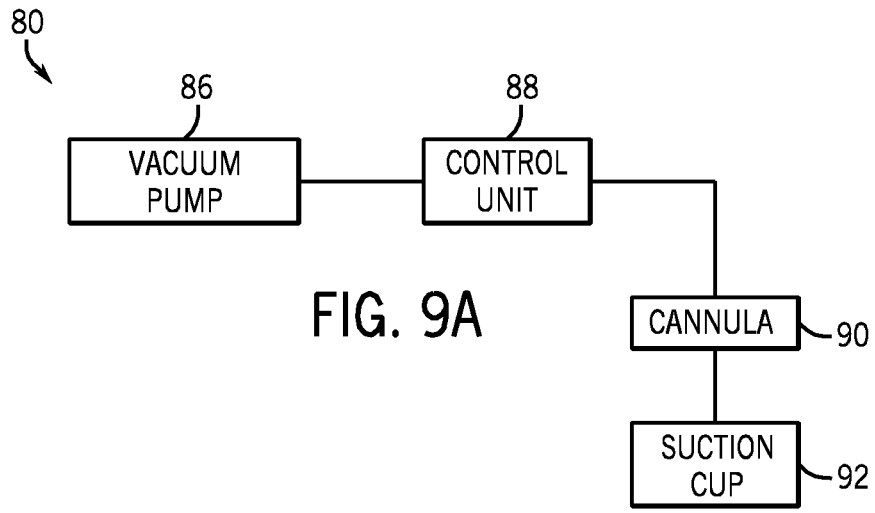
FIG. 9A depicts a block diagram of the components of an apparatus used for distending the biliary and pancreatic ducts shown in FIGS. 8A and 8B and used in the method of FIG. 7.
Figure 9B:
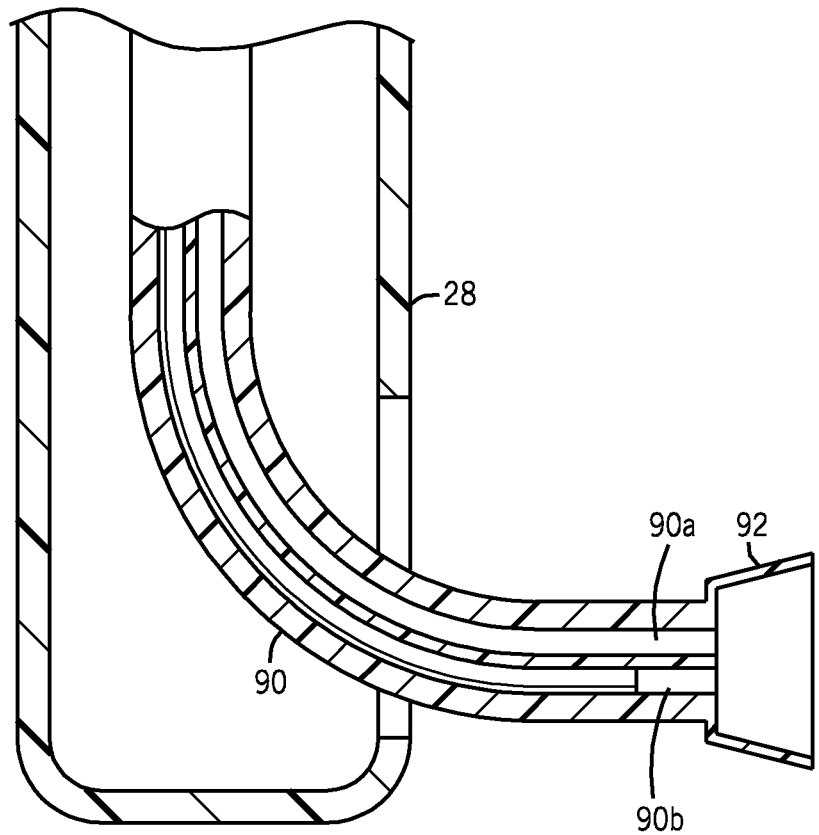
FIG. 9B depicts an enlarged illustration of the cannula of FIG. 9A.

FIG. 9A depicts a block diagram of the components of apparatus 80 used for distending the biliary and pancreatic ducts shown in FIGS. 8A and 8B and used in the method of FIG. 7. FIG. 9B depicts an enlarged illustration of cannula 90 of FIG. 9A. Apparatus 80 includes a vacuum pump 86, control unit 88 operatively coupled to vacuum pump 86 (typically using PVC), cannula 90 coupled to control unit 88 and suction cup 92, and cannula 90 to enable suction capability as well as allow a wire to advance though a wire lumen within cannula 90 and out cup 92 (into papilla 36 as described above). Note that suction cup 92 is shown as an integral part of cannula 90 but it may be permanently attached or non-permanently attached allowing removal as known by those skilled in the art. Suction cup 92 is preferably made of transparent material, such as plastic or other material, but may be made of any material suitable for ERCP as known by those skilled in the art. Vacuum pump 86 has the conventional components to provide a vacuum. Control unit 88 will have components such as a processor, memory, operating system and application software. The doctor or operator will active and deactivate the vacuum (suction) using control unit 88 as known by those skilled in the art. As indicated above, FIG. 9B depicts an enlarged illustration of cannula 90 of FIG. 9A. Cannula 90 has vacuum lumen 90a for suction capability and wire lumen 90b for a wire to advance through it.

With respect to the embodiments described above, the biliary and pancreatic ducts are physically distended to enable a wire to pass through such ducts.

Those skilled in the art know that the some of the steps of the methods described herein (e.g., advancing a cannula to subsequently achieve distention) and shown in the drawings may be performed laparoscopically. In addition, those skilled in the art, after reading this disclosure, know that devices other than an endoscope (for example) may be used for advancing a cannula to achieve the desired results. For example, certain devices may be used for laparoscopic procedures.

It is to be understood that the disclosure teaches examples of the illustrative embodiments of the present invention and that many variations of the invention can easily be devised by those skilled in the art after reading this disclosure and that the scope of the present invention is to be determined by the following claims.

What is claimed is:

1. A method of performing endoscopic retrograde cholangiopancreatography (ERCP), the method comprising:
   advancing a cannula into an opening that communicates with one or more body lumens without the cannula advancing past the opening;
   insufflating the one or more body lumens by passing gas through the cannula and into the opening to enable visualization of the one or more body lumens on an X-ray, wherein the one or more body lumens includes a biliary duct, a pancreatic duct or both the biliary and pancreatic ducts.

2. The method of claim 1 further comprising injecting contrast agent into the one or more body lumens.

3. The method of claim 1 wherein the gas is carbon dioxide.

4. The method of claim 1 wherein the gas is perfluorocarbon.

5. The method of claim 1 wherein the opening is in a wall of a duodenum.

6. The method of claim 5 wherein the advancing includes advancing the cannula through and out a distal end of an endoscope into the opening.

7. The method of claim 1 further including visualizing the one or more body lumens using an X-ray.

8. The method of claim 1 wherein the opening is in a papilla along a wall of a duodenum.

9. A method of performing endoscopic retrograde cholangiopancreatography (ERCP), the method comprising:
   advancing a cannula into an opening that communicates with one or more body lumens without the cannula advancing past the opening;
   insufflating the one or more body lumens by passing gas through the cannula and into the opening to enable visualization of the one or more body lumens on an X-ray, and wherein the one or more body lumens includes a biliary duct, a pancreatic duct or both the biliary and pancreatic ducts; and
   injecting contrast agent into the one or more body lumens.

10. The method of claim 9 wherein the gas includes carbon dioxide or perfluorocarbon.

11. The method of claim 9 wherein the opening is in a wall of a duodenum.

12. The method of claim 11 wherein the opening is in a papilla along the wall of the duodenum.

13. The method of claim 9 wherein advancing includes advancing the cannula through and out a distal end of an endoscope and into the opening.

* * * * *